United States Patent [19]

Banes

[11] Patent Number: 6,048,723
[45] Date of Patent: Apr. 11, 2000

[54] FLEXIBLE BOTTOM CULTURE PLATE FOR APPLYING MECHANICAL LOAD TO CELL CULTURES

[75] Inventor: Albert J. Banes, Hillsborough, N.C.

[73] Assignee: Flexcell International Corporation, McKeesport, Pa.

[21] Appl. No.: 09/201,570

[22] Filed: Nov. 30, 1998

Related U.S. Application Data

[60] Provisional application No. 60/067,363, Dec. 2, 1997.

[51] Int. Cl.$^7$ ....................................................... C12M 3/00
[52] U.S. Cl. .................................... 435/305.1; 435/288.3; 435/288.4; 435/305.2; 435/305.4
[58] Field of Search .............................. 435/287.1, 288.3, 435/288.4, 305.1, 305.2, 305.4

[56] References Cited

U.S. PATENT DOCUMENTS

| | | | |
|---|---|---|---|
| 4,087,327 | 5/1978 | Feder et al. | 195/1.7 |
| 4,623,355 | 11/1986 | Sawruk | 623/66 |
| 4,642,220 | 2/1987 | Björkman | 422/101 |
| 4,695,547 | 9/1987 | Hilliard et al. | 435/173 |
| 4,735,778 | 4/1988 | Maruyama et al. | 422/102 |
| 4,839,280 | 6/1989 | Banes | 435/285 |
| 4,940,853 | 7/1990 | Vandenburgh | 435/240.23 |
| 5,348,879 | 9/1994 | Shapiro et al. | 435/240.241 |

FOREIGN PATENT DOCUMENTS

| | | | |
|---|---|---|---|
| 2155948 | 10/1985 | United Kingdom | C12M 1/18 |

OTHER PUBLICATIONS

Leung et al., "Cyclic Stretching Stimulates Synthesis of Matrix Components by Arterial Smooth Muscle Cells in vitro", Science, vol. 191, Feb. 6, 1976, pp. 475–477.

Brunette, "Mechanical Strectching Increases the Number of Epithelial Cells Synthesizing DNA in Culture", J. Cell Sci. 69, 35–45 (1984).

Somjen et al., "Bone Remodelling Induced by Physical Stress is Prostaglandin $E_2$ Mediated", Biochimica et Biophysica Acta. 627 (1980) 91–100.

Banes et al., "A New Vacuum–Operated Stress–Providing Instrument That Applies Static or Variable Duration Cyclic Tension or Compression to Cells In Vitro", J. Cell Sci. 75 (1985) pp. 1–8.

Leung et al., "A New In Vitro System for Studying Cell Response to Mechanical Stimulation", Exp. Cell Res. 109 (1977), pp. 285–298.

Winston et al., "The In Vitro Response of Endothelium to Mechanical Loading", 38th ACEMB 1985, p. 88.

Winston et al., "Response of Endothelial Cells in Culture to Biaxial Deformation", Northeast Bioengineering Conference, University of Pennsylvania, 1987, 2 pp.

Thibault et al., "Mechanical Characterization of Membrane–like Biological Tissue", J. Biomechanical Engr., 1982, pp. 1–8.

*Primary Examiner*—David A. Redding
*Attorney, Agent, or Firm*—Webb Ziesenheim Logsdon Orkin & Hanson, P.C.

[57] ABSTRACT

A cell culture plate having a flexible membrane sandwiched between a base and a body. Each of the base and body have a plurality of mutually aligned openings. A wall surrounds each opening in the body thereby forming a cell culture well with a portion of the membrane functioning as the floor of the well. When a pressure differential is applied to the underside of the membrane, the membrane stretches, inducing strain on cells cultured thereon. The cell culture plate is sealingly positioned within a recess of a baseplate. An opening defined in the recess communicates with a pressure supply and provides fluid access to the cell culture plate underside to induce the pressure differential thereon.

22 Claims, 12 Drawing Sheets

FLEXIBLE BOTTOM CULTURE PLATE FOR APPLYING MECHANICAL LOAD TO CELL CULTURES

This application claims the benefit of U.S. Provisional Application Ser. No. 60/067,363 filed Dec. 2, 1997.

BACKGROUND OF THE INVENTION

1. Field of the Invention

The invention is directed toward culture plates used in the biomedical science field and, more specifically, to a culture plate having a membrane which may be flexed to stretch or compress cells in a monolayer or a three-dimensional culture adhering or tethered to the membrane.

2. Description of the Prior Art

In the human body, most cells are constantly subjected to tension and compression. Application of strain to cells in culture simulates the in vivo environment, causing dramatic morphologic changes and biomechanical responses in the cells. There are both long and short term changes that occur when cells are mechanically loaded in culture, such as alterations in the rate and amount of DNA or RNA synthesis or degradation, protein expression and secretion, the rate of cell division and alignment, changes in energy metabolism, changes in rates of macromolecular synthesis or degradation, and other changes in biochemistry and bioenergetics.

Methods of altering the mechanical environment or response of cells in culture have included wounding cells by scraping a monolayer, applying magnetic or electric fields, or by applying static or cyclic tension or compression with a screw device, hydraulic pressure, or weights directly to the cultured cells. Shear stress has also been induced by subjecting the cells to fluid flow. However, few of these procedures have allowed for quantitation of the applied strains or provided regulation to achieve a broad reproducible range of cyclic deformations.

A known device applies a defined, controlled static or variable duration cyclic tension or compression to growing cells in vitro. The device uses positive or negative pressure to deform a flexible membrane in the well of a culture plate thereby "exercising" the cells in culture and yielding up to 30% strain in the membranes. Vacuum is the preferred pressure modality. The device produces regulated strain to statically or cyclically stretch the rubber membrane and attached cells. This device is described in U.S. Pat. No. 4,789,601 issued Dec. 6, 1988 to the Applicant and is hereby incorporated by reference. With this device, the surface of the flexible membrane of the culture plate is treated to enable cells to adhere and grow thereupon. The culture plate membrane surface may include one of many materials including but not limited to genetic type I, II, III, IV collagens, elastin, fibronectin, laminen, peptides therefrom, integrin-binding peptides, compounds with amino or carboxyl functionalities, and/or combinations of peptides and proteins.

This flexing device allows users to simulate the mechanical load environment of walking, running, breathing or the beat of a heart, to cells cultured from mechanically active tissues, such as heart, lung, skeletal muscle, bone, ligament, tendon, cartilage, smooth muscle cells, endothelial cells and cells from other tissues. Rather than test the biological or biochemical responses of a cell in a static environment, the investigator can apply a frequency, amplitude and duration of tension or compression to cultured cells.

The membranes for the floors of the wells of culture dishes just described are made of blended silicone rubber. These rubber membranes are relatively thick (about three millimeters) and adhere to the side wall of the plastic culture dish by dry tack alone and are vertically supported in the culture dish by a lip extending radially from the side wall of the culture dish well. While the culture dish membrane can withstand millions of downward cyclic loadings, since it is supported by the lip and adheres to the sidewall, it may be loosened by an upward force. This is advantageous for easy removal and processing of the adherent cells. However, with this arrangement, upward cyclic loading is not permitted and the membrane can inadvertently become dislodged if such a loading is introduced.

Furthermore, while this device is satisfactory for a number of different applications, the thickness of the membrane only allows a gradient of strain upon distension by vacuum. The resulting nonuniform expansion of the membrane during use renders it less desirable than a more homogeneous strain field throughout the membrane. Additionally, this device is capable of accepting only negative pressure produced by a vacuum to deform the membrane downward but would not be amenable to positive pressure since this would tend to expel the membrane from the well. Moreover, the membrane is formed by pouring material into the wells in a culture plate and permitting it to cure. As a result, the physical shape and characteristic of each membrane could be slightly different depending upon the conditions of the individual silicone rubber lots, mixtures, pours, distribution along the culture plate sidewall, curing time and oven temperature.

In order to better control the expansion characteristics of the membrane caused by positive or negative pressures, it was desired to utilize a thin silicone membrane with or without a self-contained O-ring that fits into an O-ring cavity in the encompassing base and body of the plastic parts of the cell culture plate. The O-ring capture of the membrane permits precise pretensioning of the membrane within the well. Pretensioning prevents (1) the membrane from sagging when loaded with fluid culture medium, thus preventing cells from pooling in the well center during cell seeding, and (2) discontinuities in tension from one well to another, which would result in varying membrane strain when actively flexed. When the membrane of the prior art device was adhered to the well wall only by dry tack, such pretensioning was impossible.

An apparatus and method addressing these concerns is needed to yield reproducible unconstrained as well as constrained distension to the flexible membranes within the culture plate wells.

SUMMARY OF THE INVENTION

Accordingly, I have developed a cell culture plate that addresses the concerns of the prior art device. One embodiment of the cell culture plate of my invention includes a base having an upper surface and defining a base opening. A flexible membrane, preferably formed from a silicone material, covers the base opening and a portion of the upper surface, such that the covered opening defines a cell culture surface. A body is engaged with the base such that the flexible membrane is fixed between the base and the body. The body defines a body opening aligned with the base opening and includes a well wall extending from an upper surface of the body and surrounding the body opening. The cell culture surface and the well wall define a well. The base upper surface preferably defines a groove surrounding the base opening and the body includes a tongue extending from a lower surface of the body. The tongue matingly engages with the groove thereby fixing the flexible member between the tongue and the groove. A spacer preferably is positioned between the base and the body to maintain the body spaced apart from the base. The spacer preferably includes a post which extends through an aperture in the membrane. The post preferably is integral with either of the body or the base and is fixed to the other of the body and the base.

The base preferably defines a plurality of base openings covered by the membrane and the body preferably defines a plurality of body openings, with each body opening axially aligned with one of the base openings. Each body opening is surrounded by a well wall extending from the body upper surface and a tongue extends from the body lower surface with each base opening being surrounded by a groove matingly engaged with one of the tongues.

The body preferably further includes a side wall surrounding the well walls. At least one body rib extends between outer surfaces of a pair of the well walls and at least one body rib extends between an outer surface of one well wall and the side wall.

A plurality of support walls preferably extends from a lower surface of the base. Each support wall surrounds one of the base openings. A base wall surrounds the support walls and at least one rib extends between outer surfaces of a pair of the support walls and at least one rib extends between an outer surface of one support wall and the base wall.

A second embodiment of the present invention further includes a cell culture well having an annular member defining a chamber and including a wall, a top surface and a base. A flexible membrane extends across the top surface. A plate defining an opening overlies the flexible member and is attached to the annular member. A sealing ring preferably is disposed in a groove in the top surface. A plurality of fasteners extends through the plate and into the top surface. The base preferably defines an aperture aligned with the opening. A tube preferably extends through the wall and is in fluid communication with the chamber. The tube is adapted to be connected to a pressure supply, such that when a pressure differential is provided from the pressure supply, the flexible membrane is stretched. When the pressure supply is a vacuum source and a negative pressure is provided, the flexible membrane is stretched downwardly. If the pressure supply is positive pressure, the flexible member is deformed upward.

A third embodiment of the present invention includes a cell culture plate assembly having a cell culture plate including (i) a base having an upper surface and defining a base opening; (ii) a flexible membrane covering the base opening and a portion of the upper surface, the covered opening defining a cell culture surface; and (iii) a body engaged with the base such that the flexible membrane is fixed between the base and the body, wherein the body defines a body opening aligned with the base opening and includes a well wall extending from an upper surface of the body and surrounding the body opening, whereby the cell culture surface and the well wall define a well.

A baseplate defining a recessed portion having a bottom surface with a central opening therethrough receives the cell culture plate in a sealing fit. The baseplate further defines a port and a passageway through the baseplate in fluid communication with the port and the central opening. A gasket preferably surrounds the cell culture plate, the gasket being sealingly fitted within the recess.

The baseplate of the cell culture plate assembly preferably defines a plurality of the recessed portions wherein the central opening in each recessed portion is equidistantly located from the port. The assembly preferably further includes a plurality of the cell culture plates with each cell culture plate sealingly fitted within one of the recesses along with a plurality of cell culture lids, each lid being sized to fit over one of the cell culture plates. The port is adapted to be connected to a pressure supply, such that when a pressure differential is provided from the pressure supply, the cell culture surface is stretched. When the pressure supply is a vacuum source and a negative pressure differential is provided, the flexible cell culture surface is stretched downwardly. When the pressure supply is a positive pressure source, the flexible cell culture surface is stretched upwardly.

A complete understanding of the invention will be obtained from the following description when taken in connection with the accompanying drawing figures wherein like reference characters identify like parts throughout.

DETAILED DESCRIPTION OF THE PREFERRED EMBODIMENTS

Figure 1A:
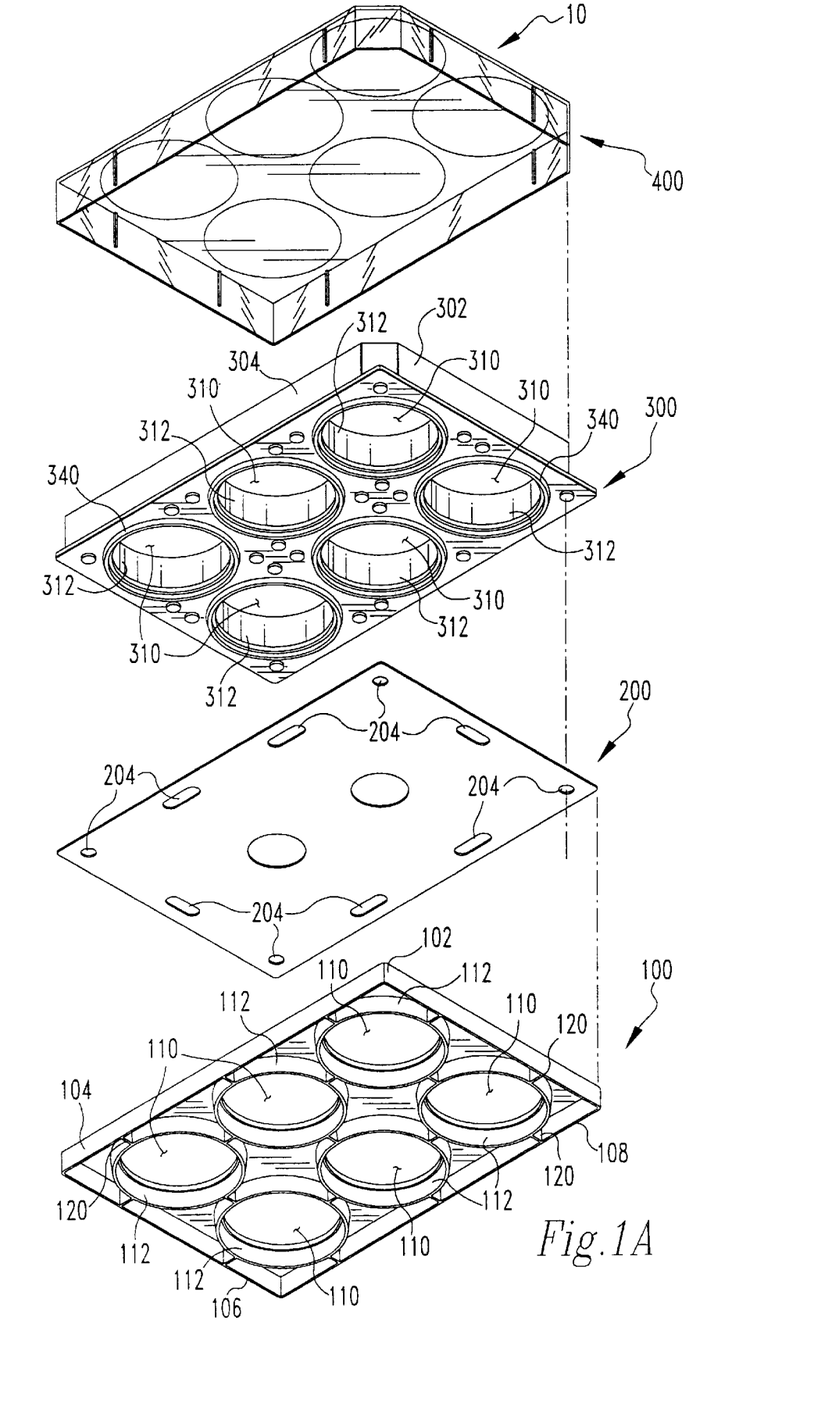
FIG. 1A is an exploded perspective view of the underside of one culture plate made in accordance with a first embodiment of the present invention including a base, a membrane, a body and a lid.

FIG. 1A illustrates an exploded perspective of a culture plate 10 with flexible well bottoms made in accordance with the subject invention. Generally speaking, the culture plate 10 is made up of a base 100, a membrane 200, a body 300 and a lid 400. As will be discussed in further detail, the base 100 is secured by sonic welding or heat staking against the body 300, thereby compressing and securing the membrane 200 therebetween.

FIGS. 2–5 illustrate the base 100 shown in FIG. 1A. The base 100 includes four sides 102, 104, 106, 108 which generally define a rectangle. The base 100 defines a plurality, and preferably six, of equispaced, base openings 110 surrounded by cylindrical support walls 112 extending from a lower surface of the base 100. A planar layer 114 defines a top surface of the base 100. A plurality of ribs 120 (FIG. 3) interconnect the cylindrical walls 110 to the four sides 102, 104, 106, 108 and to one another, thereby providing structural stiffness to the base 100. The placement and structural characteristics of the ribs 120 are crucial to prevent flexing of the base 100 and the body 300 during use.

Figure 2:
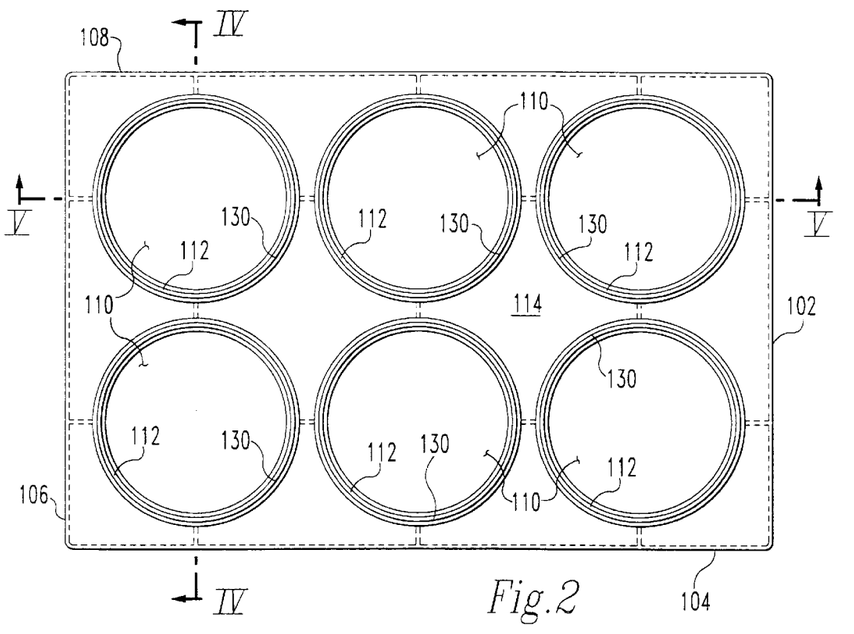
FIG. 2 is a top view of the base shown in FIG. 1A.
Figure 3:
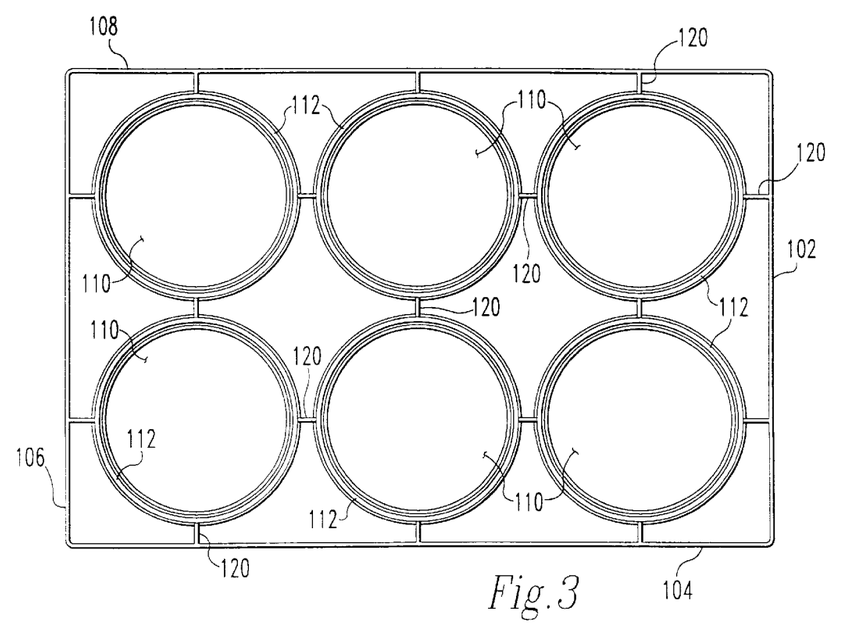
FIG. 3 is a bottom view of the base shown in FIG. 2.
Figure 4:
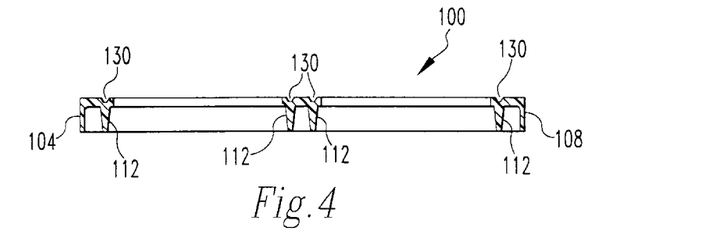
FIG. 4 is a sectional view of the base shown in FIG. 2 taken along line IV—IV.
Figure 5:
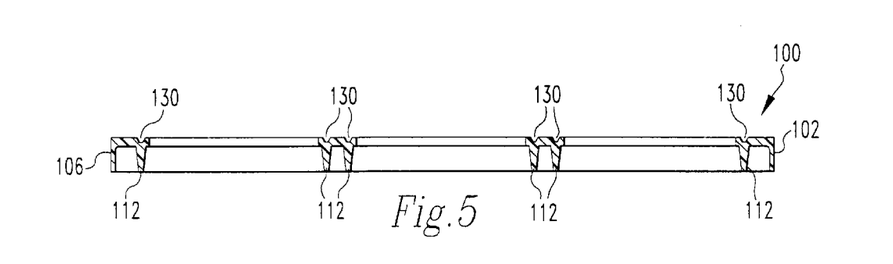
FIG. 5 is a sectional view of the base shown in FIG. 2 taken along line V—V.

As shown in FIGS. 2, 4 and 5, a groove 130 is defined in the planar layer 114 of the base 100 on an opposite side of the base 100 from each cylindrical support wall 112. The grooves 130 are each aligned on the opposite side of the planar layer 114 with the cylindrical support walls 112.

Figure 6:
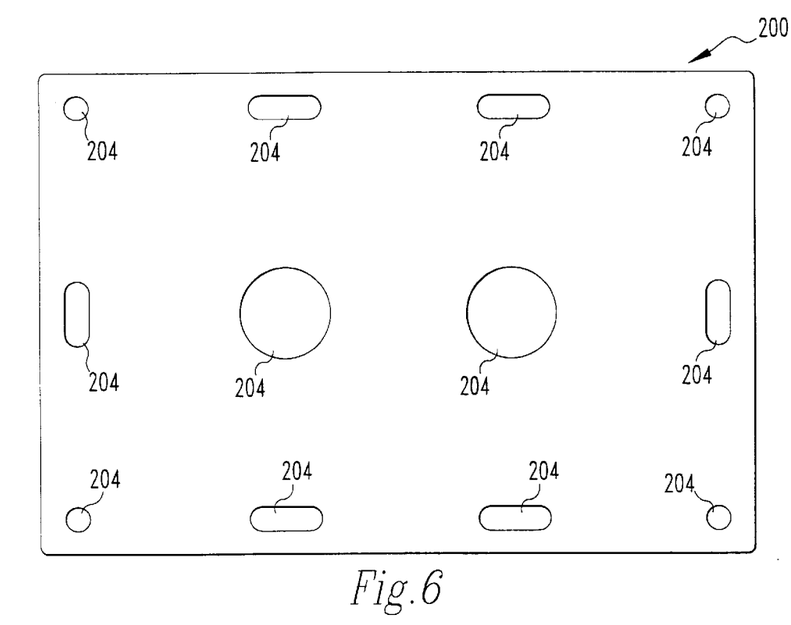
FIG. 6 is a plane view of the membrane shown in FIG. 1A.

FIG. 6 depicts a plan view of the membrane 200. The membrane 200 defines a plurality of apertures 204 which are used to secure the body 300 to the base 100 as described in detail below. The membrane 200 may be formed from a transparent silicone or urethane material prepared as a molded and calendered sheet such as a material produced by the Bisco Company identified as Product No. HT6240. The characteristics of the silicone membrane are such that creep is nominal with low percent elongation, even for millions of flexation cycles. The membrane 200 may be made in accordance with material specification 35 SHORE A. The thickness of the membrane is approximately 0.5 millimeter (0.020 inch) and the membrane material is pliant and resilient so as to act as a seal between the base 100 and the body 300. The membrane material should also provide the specific physical properties of composition, surface properties, clarity and homogeneity in all parameters, especially in the elasticity necessary to elongate the membrane 200 such that the culture and cells attached thereto may be deformed in a controllable and reproducible manner. The silicone rubber forming the membrane 200 may be chemically modified to accommodate cell growth. Furthermore, the transparent silicone material does not significantly distort the image of the cells as did the thicker membrane material used in devices of the prior art. Therefore, cells can be viewed directly on the membrane with a conventional inverted phase microscope used for examination of cultured cells. Instead of being cultured directly on the membrane 200, cells may be cultured in a three-dimensional flexible growth substrate (not shown) covering the membrane 200.

Figure 1B:
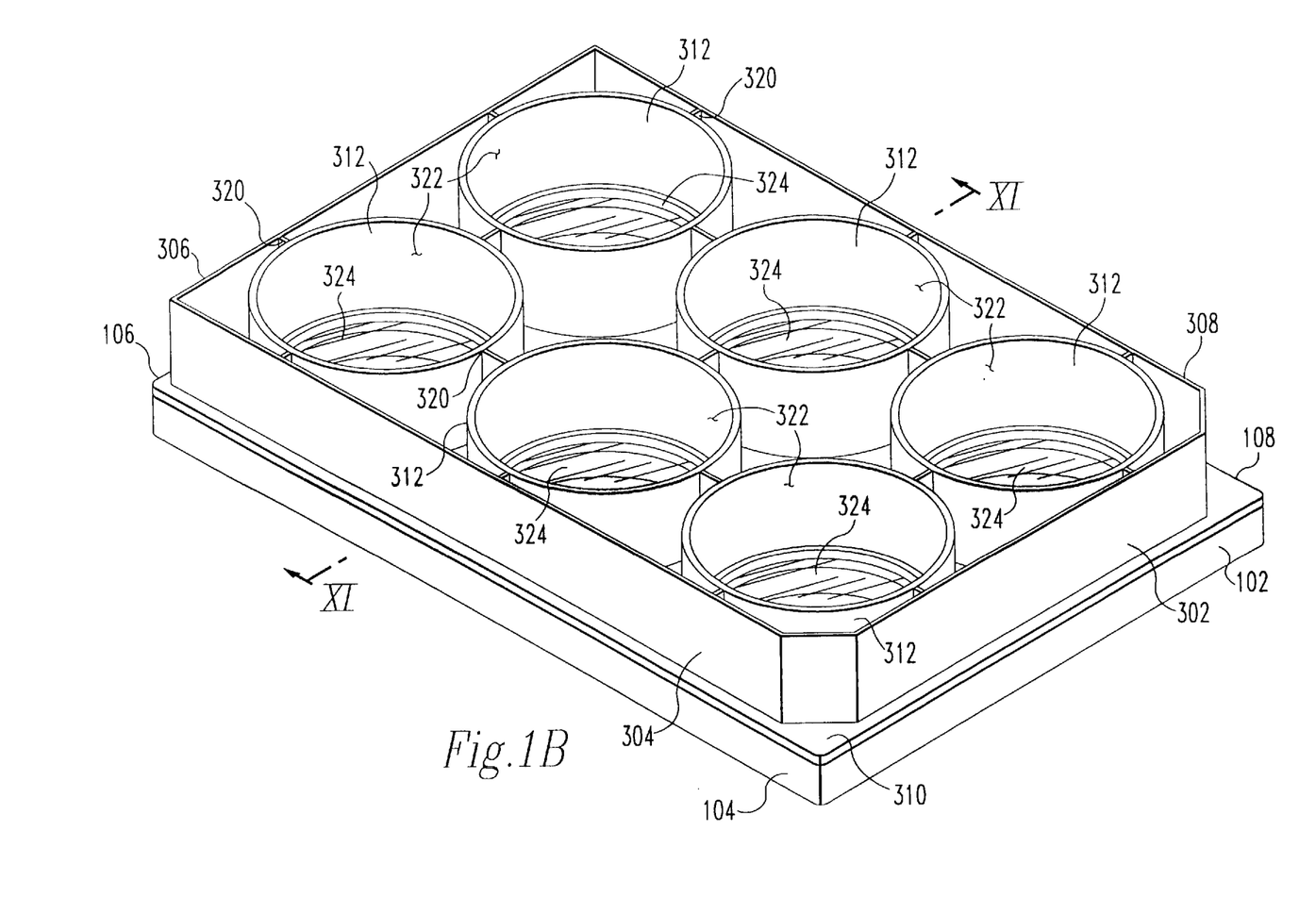
FIG. 1B is a top perspective view of the culture plate shown in FIG. 1A as assembled without the lid.
Figure 7:
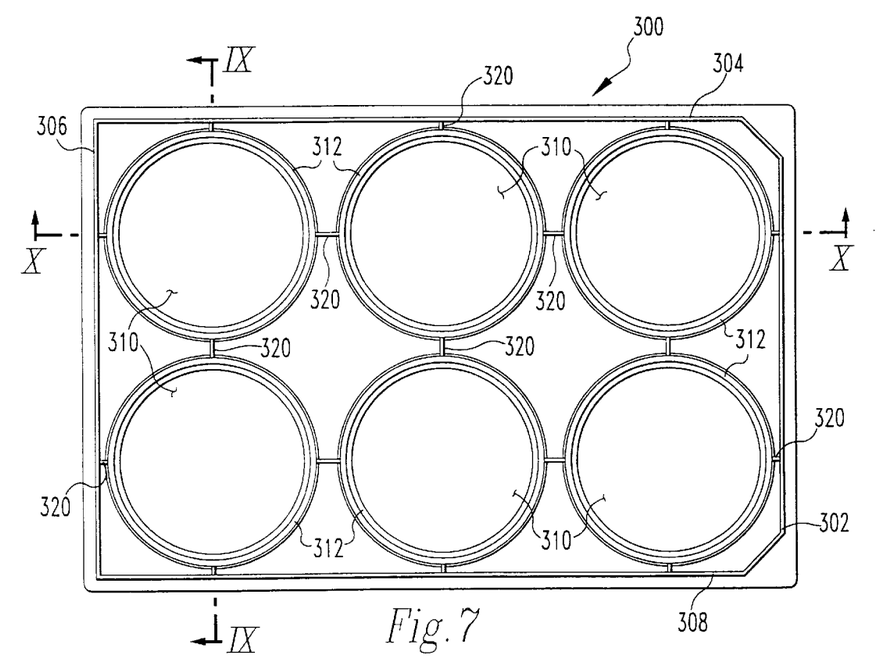
FIG. 7 is a top view of the body shown in FIG. 1A.

FIG. 7 shows a top view of the body 300. Paralleling the structure of the base 100 and as shown in FIGS. 1A, 1B and 7, the body 300 has side walls 302, 304, 306, 308 generally defining a rectangular shape. A ledge 310 extends around a perimeter of the body 300. The body 300 likewise defines a plurality of, preferably six, equispaced openings 310 surrounded by cylindrical well walls 312 and interconnected by ribs 320 with one another and the side walls 302, 304, 306 and 308. The ribs 320 provide strength to the culture plate so that when positive or negative pressures are applied to the device, only the membrane is deformed, and the plastic body 300 does not bend.

When the culture plate is assembled as depicted in FIG. 1B, the cylindrical support walls 112 of the base 100 are aligned with the cylindrical well walls 312 of the base 300 and the membrane 200 is sealingly sandwiched therebetween. In so doing, the membrane 200 is divided up by the cylindrical walls 310 to define individual wells 322 and floors 324. The wells 322 defined by the cylindrical walls 312 and the floors 324 are adapted to accept culture fluid such that cells may grow on the floors 324.

Just as the base 100 has grooves 130 defined in the planar layer 114 to secure the membrane 200, the body 300 has a protruding tongue 340 (FIG. 8) projecting from an underside of the body 300 to secure the membrane 200. As will be discussed hereinafter in more detail, the tongue 340 is adapted to press against the membrane 200 and mate with the grooves 130 of the base 100 so as to seal and stretch the membrane 200, thereby precisely and reproducibly pretensioning the floor 324 of each of the wells 322. The geometry and dimensions of the tongue 340 and groove 130 system are important to stable membrane capture. The clamped membranes should withstand millions of cycles of deformation without compromising the membrane pretension or the seal.

Figure 8:
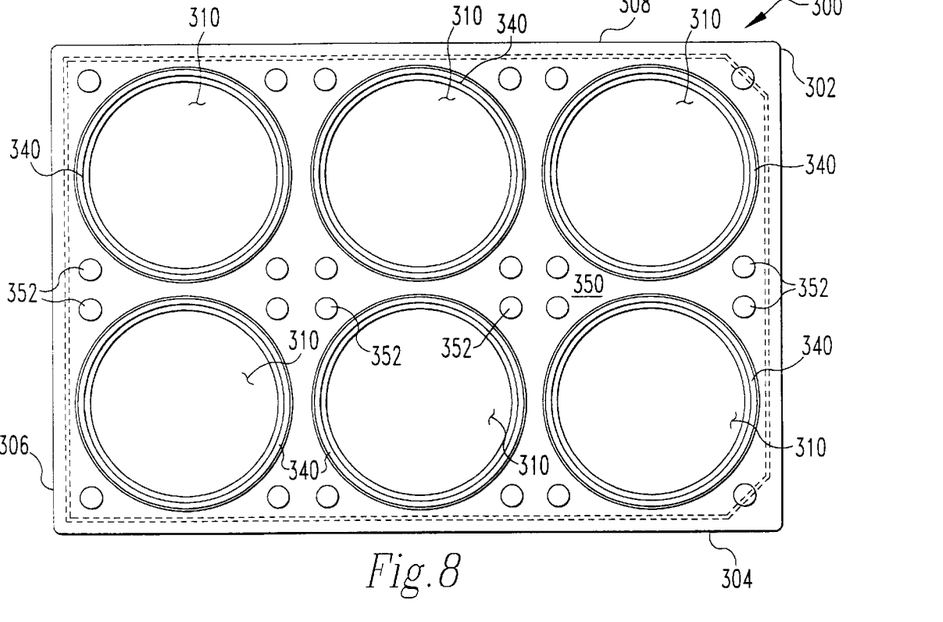
FIG. 8 is a bottom view of the body shown in FIG. 7.
Figure 9:
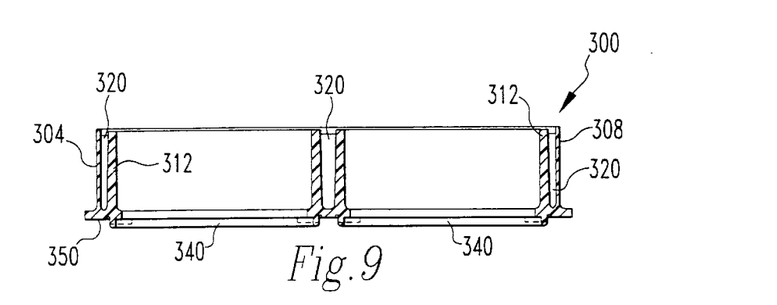
FIG. 9 is a sectional view of the body shown in FIG. 7 taken along line IX—IX.
Figure 10:
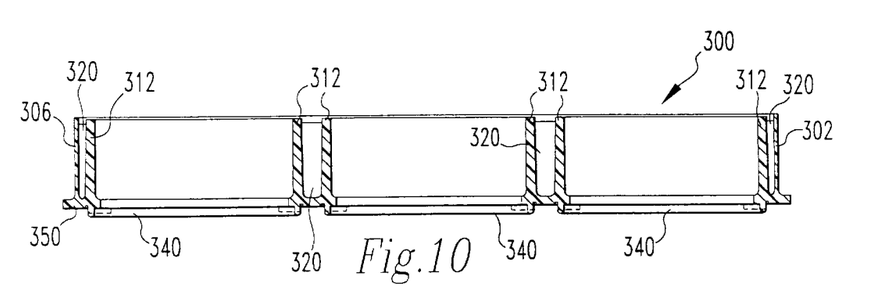
FIG. 10 is a sectional view of the body shown in FIG. 7 taken along line X—X.

Referring to FIGS. 8–10, the body 300 also includes a planar layer 350 from which extends a plurality of weld posts 352 which are adapted to be fixed to the base 100 as described in more detail below. The weld posts 352 are depicted in FIG. 8 as being positioned in a particular patterned arrangement, but other arrangements of the weld posts 352 are possible.

Figure 11:
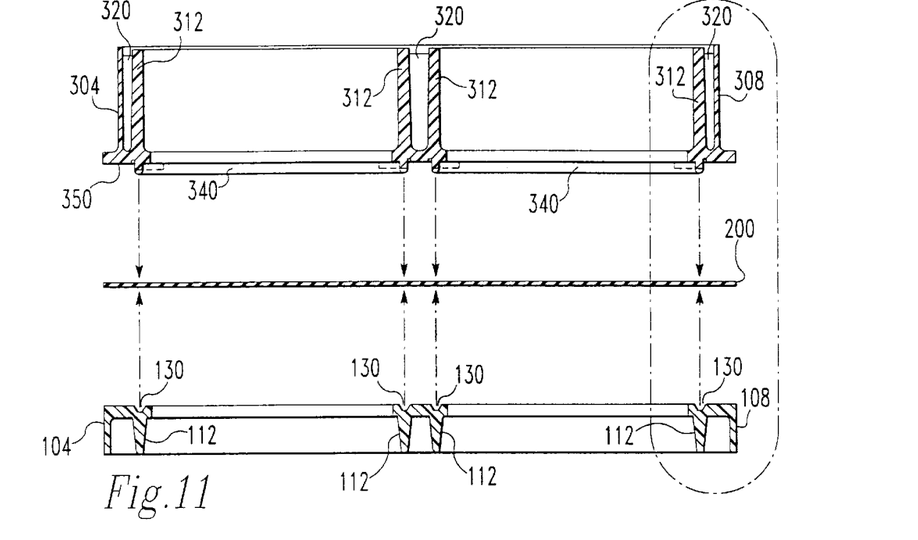
FIG. 11 is an exploded sectional view of the body, base and membrane shown in FIG. 1B taken along line XI—XI.

FIG. 11 illustrates an exploded end view of the body 300, membrane 200 and base 100 prior to assembling the culture plate. The tongues 340 in the body 300 are aligned with the grooves 130 in the base 100 such that when the body 300 is pressed against the base 100, the membrane 200 is forced into the grooves 130 by the tongues 340. To secure the body 300 to the base 100, the two pieces are pressed together, thereby sandwiching the membrane 200 therebetween. The apertures 204 through the membrane 200 align with the weld posts 352 on the body 300 such that each weld post 352 extends through one of the apertures 204 and contacts the planar layer 115 of the base 100 and not the membrane 200. This serves a two-fold purpose. First of all, the weld posts 352 act as spacers to avoid the possibility of pressing the tongues 340 against the membrane 200 with excessive force. The weld posts 352 bottom out on the planar layer 115 of the base 100, thereby limiting such a force. The weld posts 352 in the body 300 are fused to the base 100 preferably via a sonic welding process. Alternatively, heat staking may be used which involves advancing a high temperature lance through the weld posts 352 such that the material of the weld posts 352 fuses with the material of the base 100. The weld posts 352 act as energy directors that are strategically placed so that the base 100 and the body 300 can be aligned, pre-clamped with a precise amount of clamping force, then welded together using heat staking.

The base 100 and the body 300 may be made of a blended polystyrene composition or other plastic material which is resistant to cracking. Particularly, the material used to mold the base 100 and the body 300 must resist fracture upon pre-clamping and sonic welding. The preferred materials are a blend of virgin grade A polystyrene and a rubberized material that allows some flexibility in the base 100 and the body 300 to withstand the vibration that results from sonic welding. However, if the base 100 and the body 300 are to be attached by heat staking, materials tolerant of this process should be used.

The culture plate wells 322 are defined by the cylindrical walls 312 in the body 300 and not by the cylindrical walls 112 in the base 100. One purpose of the cylindrical walls 112 in the base 100 is to provide a backing for the grooves 130 such that when the tongues 340 are forcefully urged against the membrane 200 into the grooves 130, the planar layer 114 of the base 100 will possess the rigidity necessary to accept the tongue 340 without flexing. Additionally, the cylindrical walls 112 of the base 100 provide stability to the base 100 when positive and negative pressures are introduced to the membrane 200 from the underside of the base 100. Another feature of the configuration of the base 100 is that the base openings 110 are of dimensions and configurations to accept a valved rubber bung which can be used to close off a given well in the six well culture plate to prevent flexing of that well.

Figure 12:
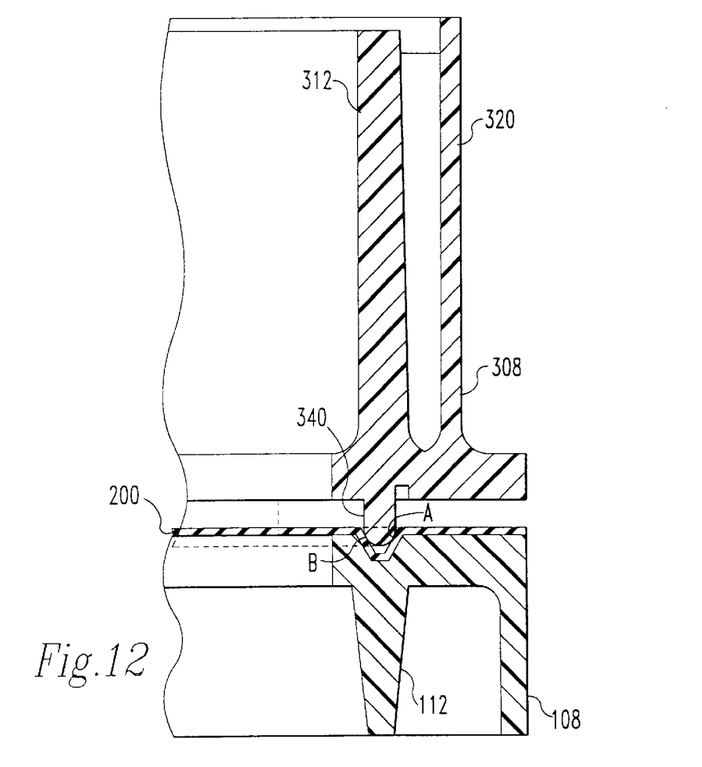
FIG. 12 is an enlarged sectional view of the encircled portion of FIG. 11 with the parts assembled.

The arrangement for sealing the membrane 200 against the body 300 is more clearly illustrated in FIG. 12 which shows the encircled portion of FIG. 11 with the components in an assembled position. The grooves 130 may be generally V-shaped and the tongues 340 generally rounded such that the membrane 200 is clamped against the walls of the V at two positions A, B defining two circles, one defined by A on the inside half of the tongue 340/groove 130 arrangement and the other defined by B on the outside half of the tongue 340/groove 130 arrangement. This, in essence, provides two seals of the membrane 200 within the groove 130. These seals are circumferential and define two annuli, one on either side of the tongue 340. Alternatively, the flexible membrane 200 may be molded to include an integral O-ring (not shown) which fits into a groove in the base 100 or the body 300.

This arrangement also produces an additional benefit. In order to create a culture plate in which one or all of the well floors 324 are pretensioned, it is necessary to stretch the membrane 200 in a defined fashion. The membrane 200 compressed between the tongues 340 of the body 300 and the grooves 130 of the base 100 is forced to stretch to conform to the grooves 130. The grooves 130 have excess space beneath the tongues 340 to receive membrane 200 material that may be compressed into the grooves 130. By doing so, the membrane 200 must expand and is pretensioned. When the membrane 200 is approximately 0.01 inch thick it may be deformed by extending the tongue 340 about 0.0144 inch into a groove 130 having a depth of about 0.038 inch. If the groove 130 is deeper so that the tongue 340 sits lower in the groove 130, the resulting tension on the membrane 200 is greater. The groove/tongue arrangement therefore produces a capture mechanism which not only secures the membrane 200 against the body 300 but does so in a fashion that pretensions the membrane 200 so the membrane remains essentially planar under a load of at least four grams of culture fluid and cells.

It should be appreciated that, while not illustrated, other methods for securing the membrane 200 between the body 300 and the base 100 may be utilized. As examples, adhesives, sonic welding or mechanical fastening techniques may be used. However, it must be kept in mind that the force of the tongues 340 against the grooves 130 must be maintained at a minimum and a uniform clamp force to ensure the integrity of the seal without cutting the membrane upon clamping it or chafing or cutting it during active flexing. For that reason, weld posts 352 along the planar layer 350 of the body 300, in as many locations as possible without affecting the integrity of the structure, are desired. While the weld posts 352 are illustrated on the planar layer 350 of the body 300, it is entirely possible for such weld posts 352 to be on the planar layer 114 of the base 100 (not shown).

The ribs 120, 320 on the base 100 and body 300, respectively, are provided to enhance the structural stiffness of the culture plate 10. The weld posts 352 and the heat stake method of fusing the weld posts 352 are intended to rigidly mate the base 100 and body 300 to provide further stiffness to the culture plate 10. While such stiffness may not be needed in culture plates having a rigid membrane which is not intended to flex and, therefore, will not be subjected to a differential pressure, when the membrane is flexible and deformed by a pressure differential, such stiffness becomes important to the structural integrity of the culture plate and also for the ability to determine the true deflection of the membrane. If the respective planar layers 114, 350 of the base 100 and the body 300 also deflect, then the true deflection of the well floors 324 would be difficult to determine.

It should further be appreciated that the goal of the arrangement depicted in FIG. 12 is to seal and to stretch the membrane 200 within the well 322. There may be geometrical configurations other than the tongue and groove system through which the body 300 may mate with the base 100 to secure the membrane 200 and provide a similar result. Furthermore, the tongue 340 and groove 130 as described may be interchanged so that the tongue 340 is part of the body. The ledge 310 also provides a clamping surface against which a clamping mechanism (not shown) may bear to seal together the base 100 and the base 300, particularly during appreciation of positive pressure to the culture plate 10.

Figure 13:
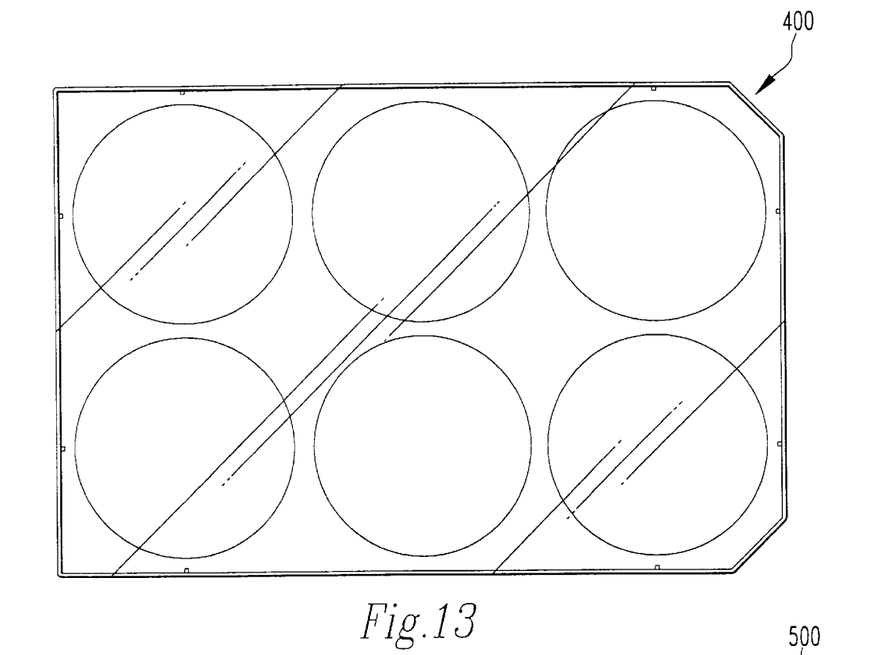
FIG. 13 is a top view of the lid shown in FIG. 1A.

FIG. 13 illustrates a top view of the lid 400 shown in FIG. 1. The lid 400 is not critical to the invention but may be placed over the wells 322 and seat on the ledge 310 to provide protection to the cells against microbial contamination. The lid preferably is made of a transparent material.

Figure 14:
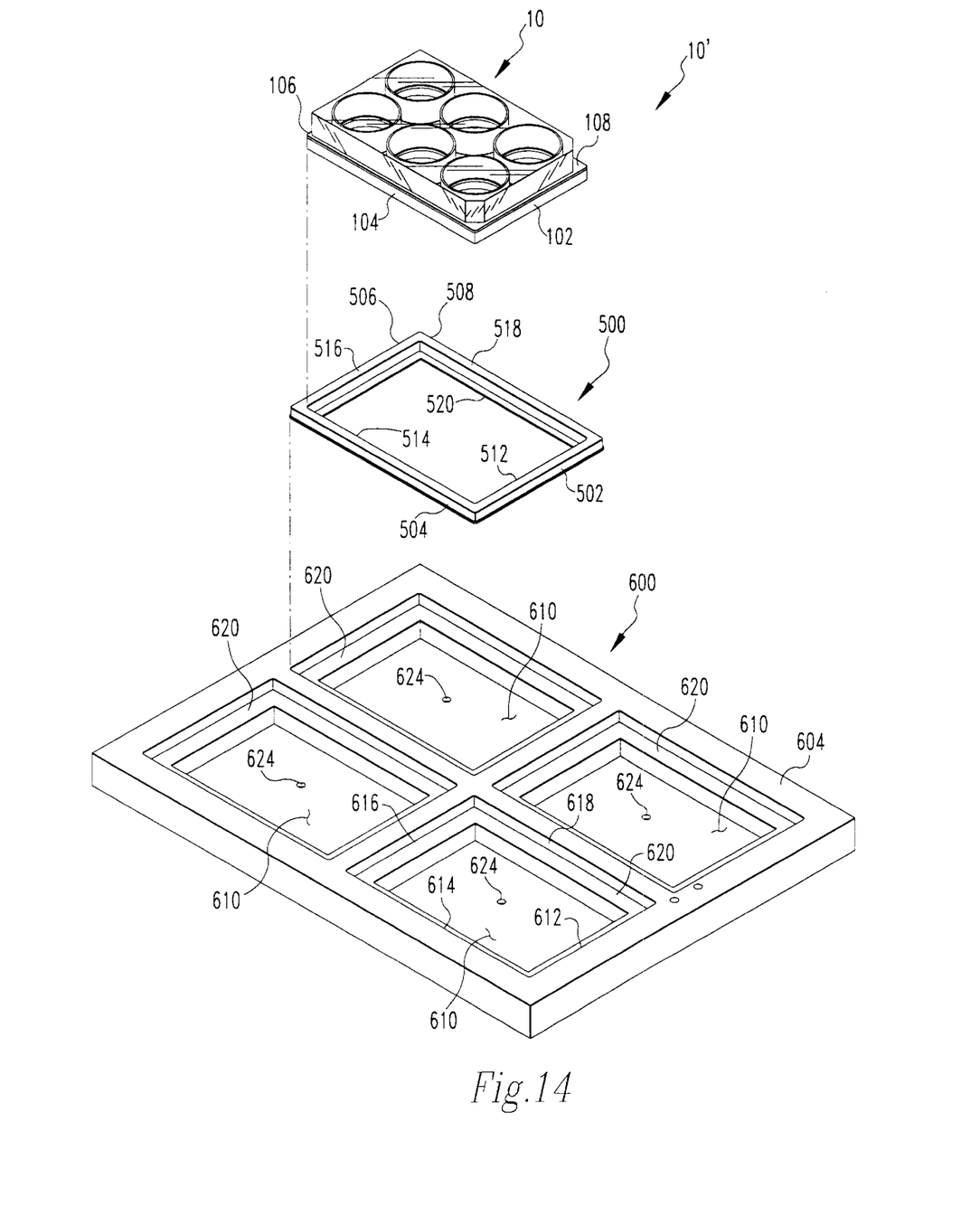
FIG. 14 is an exploded perspective view of a baseplate assembly which receives the cell culture plate shown in FIG. 1B with a gasket.
Figure 15:
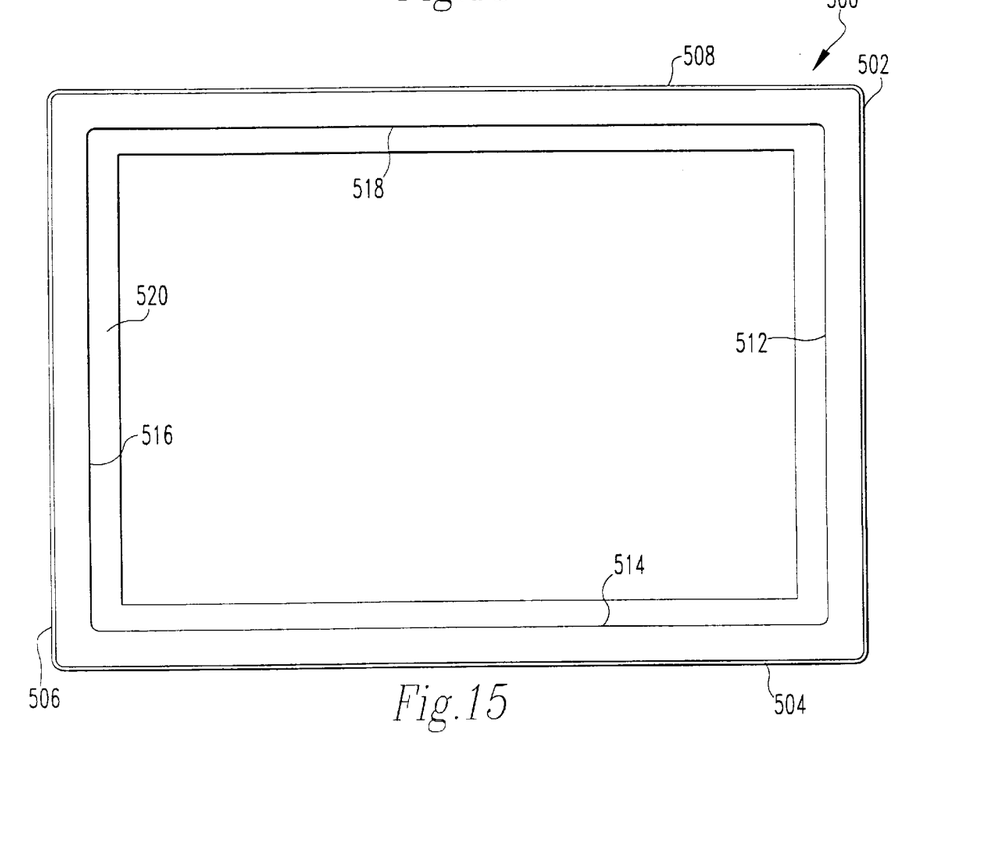
FIG. 15 is a top view of the gasket shown in FIG. 12.
Figure 16:
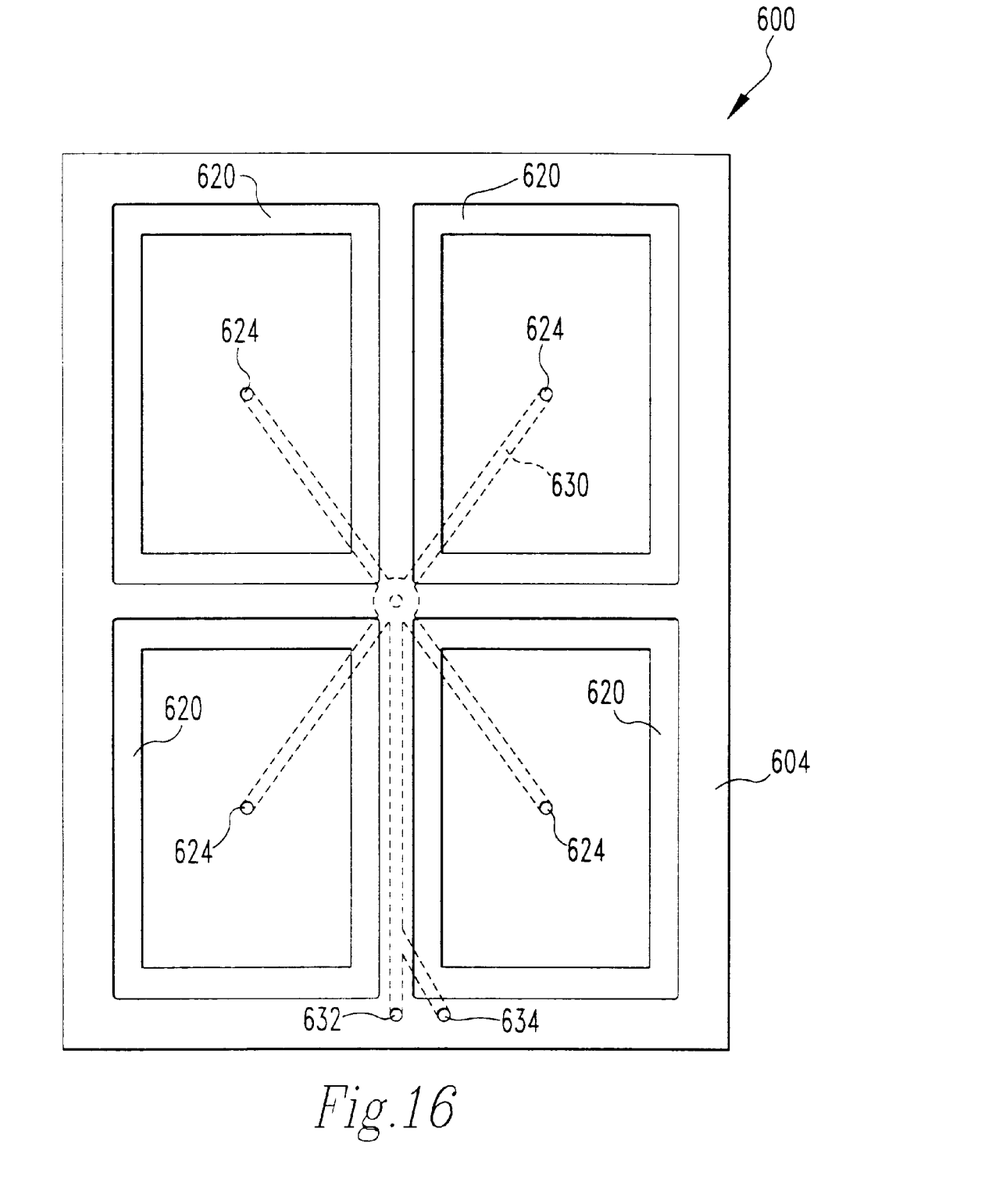
FIG. 16 is a top view of the baseplate shown in FIG. 12.

The membrane 200 in the culture plate 10 may be flexed by applying a pressure differential to the underside of the floors 324. In this manner the cells attached to the upper side of the floors 324 are stretched as desired. Referring to FIGS. 14–16, the membrane 200 is flexed by incorporating the cell culture plate 10 in an assembly 10' including at least one gasket 500 and a baseplate 600. While only a single culture plate 10 is illustrated in FIG. 14, it should be appreciated that the assembly 10' may accommodate up to four or more culture plates.

The sidewalls 102, 104, 106, 108 of the base 100 of the culture plate 10 have smooth outer surfaces which are surroundable by a flexible gasket 500 having outer walls 502, 504, 506 and 508 as depicted in FIGS. 14 and 15. Inner walls 512, 514, 516, 518 of the gasket 500 mate with the side walls 102, 104, 106, 108, respectively, of the culture plate base 100 to provide a snug fit. An inwardly extending lip 520 is positioned at a bottom of the gasket 500 and acts as a seating surface for the culture plate 10. The gasket 500 may be made of rubber or any other pliable material that typically is used as a sealing gasket in industry, such as molded natural gum rubber in accordance with 50 SHORE A.

As depicted in FIG. 14, the baseplate 600 includes a body 604 defining a plurality, and preferably four, of generally rectangularly shaped recessed portions 610 defined by four walls 612, 614, 616 and 618. The outer walls 502, 504, 506, 508 of the gasket 500 form a generally rectangular shape which is slightly smaller than the recessed portions 610 defined in the body 604 of the baseplate 600. The walls 612, 614, 616 and 618 extend partially into the thickness of the baseplate 600 to a positioning ledge 620 upon which the gasket 500 seats rest.

Figure 17:
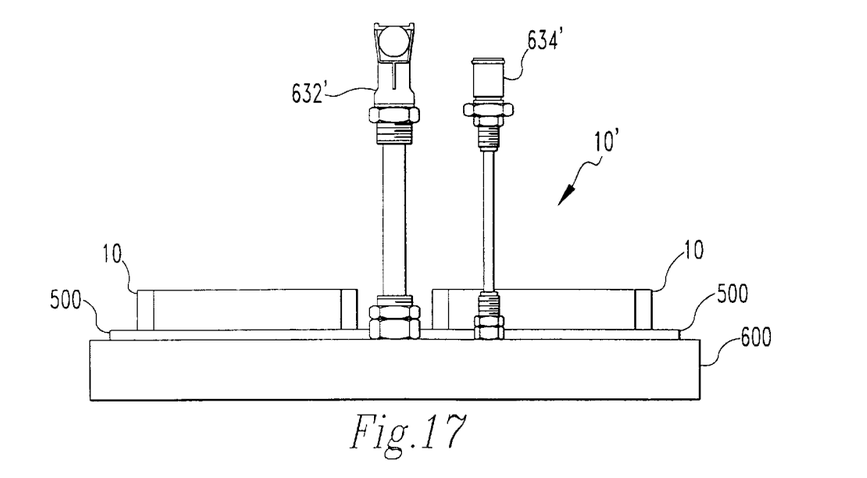
FIG. 17 is a side view of the baseplate assembly showing pressure supply lines.

As depicted in FIG. 16, the body 604 of the baseplate 600 defines a branched passageway 630. The passageway 630 extends between a central opening 624 defined in each of the recessed portions 610 of the body 604 and a pair of supply portals 632 and 634. A pair of pressure supply lines 632' and 634', shown in FIG. 17, are connected to the supply portals 632 and 634, respectively. For convenience, one line 632' is provided with a male connector while the other line 634' is provided with a female connector. In this fashion, a pressure differential applied to the supply lines 632' and 634' will be transmitted through the passageway 630 to the underside of the culture plate 10, thereby flexing the well floors 324 as appropriate. One of the lines 632' and 634' preferably is connected to a pressure transducer (not shown) to gauge the amount of pressure applied to the culture plate 10. A second pressure transducer (not shown) is positioned in the other line near the baseplate 600 to measure the actual pressure delivered to the culture plate 10. The pressure delivered may be adjusted based on any differences between the readings at the two pressure transducers.

Although it is not illustrated in FIG. 14, it should be appreciated that each of the four rectangular recessed portions 610 in the baseplate 600 is intended to accommodate a culture plate 10 and in the event a culture plate 10 does not occupy a recessed portion 610, then the opening 624 to the passageway 630 should be sealed at that location with a bung, screw or valve.

FIG. 16 illustrates that the distance from any one supply line portal 632, 634 to any opening 624 within a recessed portion 610 is uniform. In order to produce a simultaneous uniform motion of each well floor 324 in response to a pressure differential introduced by the supply lines, it is important for these distances and volumes to be equal. If they were not, for example, the culture plate 10 situated in one recessed portion 610 would experience a pressure differential a short time before or after a culture plate 10 in another recessed portion 610, and the motion of the associated well floors 324 would be out of phase with one another.

Returning to FIG. 12, the cylindrical wall 112 of the base 100 defines a volume beneath membrane 200 which is intentionally shallow. The membrane 200 will be flexed using pressure differential and this differential will be produced by a gas, such as air, hence, some compression of the gas is inevitable and this will affect the response time of the membrane 200. To minimize this response time, the volume of the cavity beneath the membrane 200 is made small, reducing the volume of gas that is compressed or suctioned and thereby reducing the response time of the membrane 200. The pressure differential applied to cause the membrane 200 to flex may be positive pressure or negative pressure (evacuation). In addition, one may incorporate the opposite pressure to aid in draining a membrane to the neutral, planar position. When a vacuum is the principle deforming pressure on the deformation stroke, a positive pressure may be introduced for the release stroke. For positive pressure as the principle deformation pressure, a vacuum may be introduced during the release stroke. In this way the response time of the membrane may be reduced. In addition, the shape of the waveform describing the pressure differential and membrane deformation may be precisely controlled.

Figure 18:
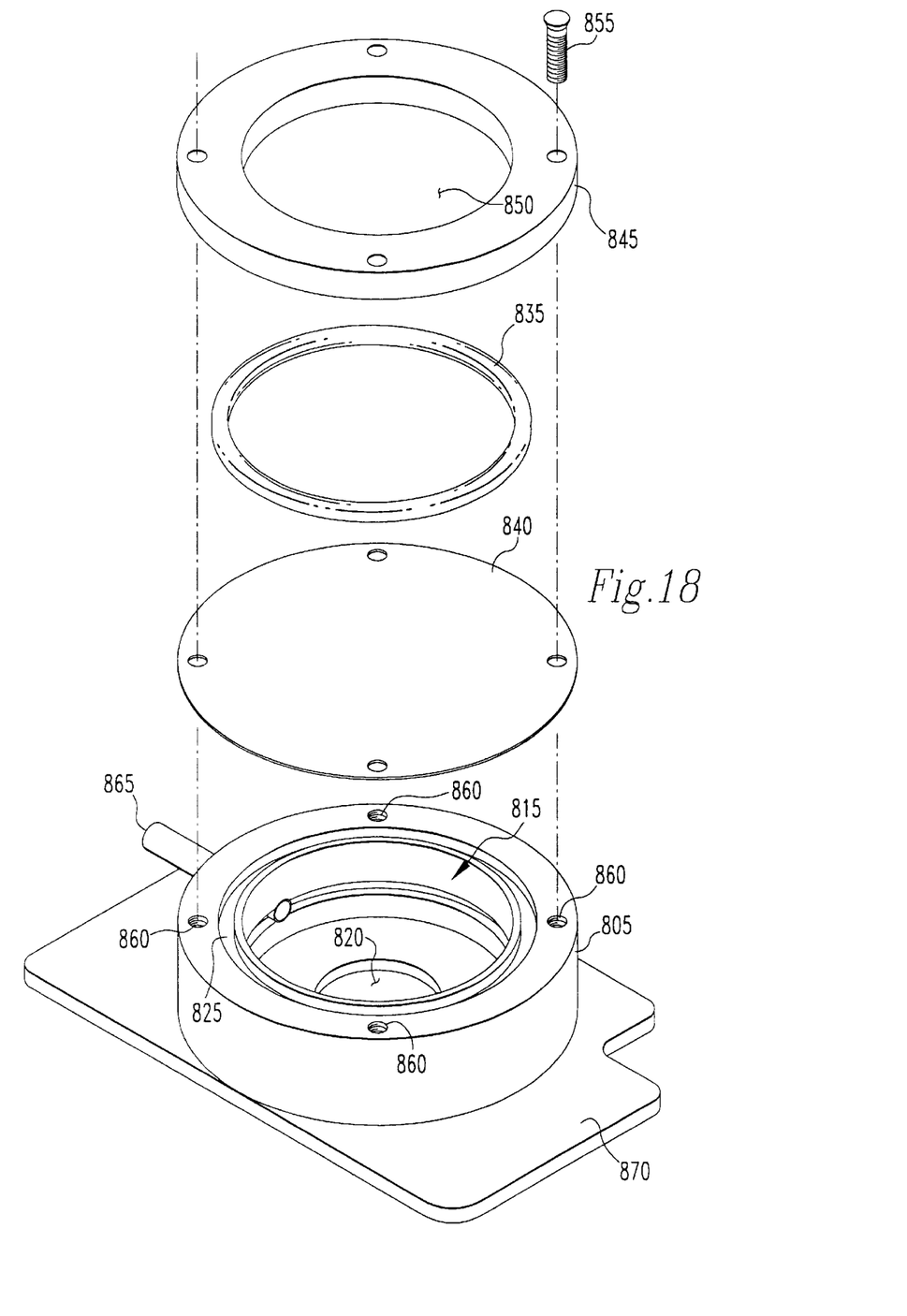
FIG. 18 is an exploded perspective view of a single well culture plate made in accordance with a second embodiment of the invention.
Figure 19:
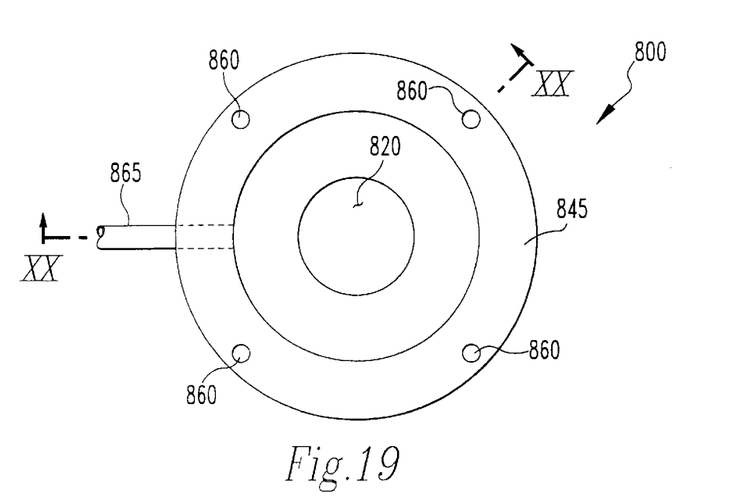
FIG. 19 is a top view of the single well culture plate shown in FIG. 18.
Figure 20:
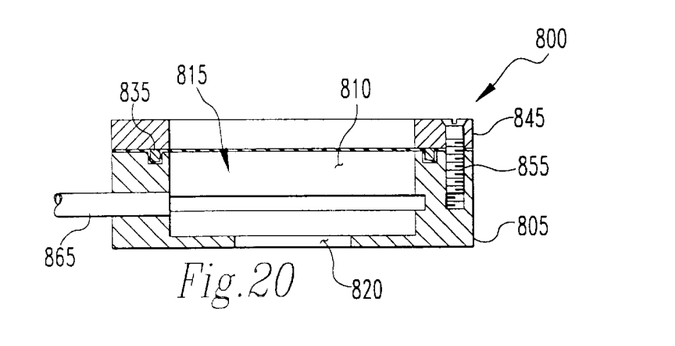
FIG. 20 is a sectional view of the single well culture plate shown in FIG. 19 taken along line XX—XX.

While what has so far been discussed is a device for the flexing of multiple membranes in a multi-welled culture plate, it is entirely possible to incorporate the elements of this invention into a single membrane and single well device. FIGS. 18–20 illustrate a single well culture plate 800 including a cylindrical body 805 having a bore 810 of a first diameter extending partially through the body 805 and defining a cylindrical well 815 and having a bore 820 of a second diameter which is equal to or smaller than the first bore 810 diameter and extends through the remainder of the body 805. The bottom of the device may have a plate that fits a stage micrometer that holds the device to the stage. In addition, this plate may have a central cylindrical portion aligned with the bore 820 that is transparent to allow white light to illuminate the specimen (cells) grown on the membrane above. This embodiment may be used to visualize cells under active flexation with a white light, fluorescence or scanning confocal microscope. A circular groove 825 is defined in a planar top surface 830 of the body 805 and is sized to accept a sealing gasket 835 such that at least a portion of the sealing gasket 835 protrudes beyond the planar top surface 830.

A flexible membrane 840, of a material similar to that used in the culture plate 10 described above, is placed on the planar top surface 830 of the body 805 and the sealing gasket 835 is positioned over the membrane 840 and aligned with the circular groove 825. A cylindrical plate 845 having a bore 850 extending therethrough is placed over the sealing gasket 835 against the membrane 840. The plate 845 clamps the sealing gasket 835 against the membrane 840 and is secured to the top surface 830 of the body 805 using conventional means such as a plurality of screws 855 (only one being shown) mounted about its perimeter and engaging mating holes 860 defined in the body 805. The plate 845 preferably has a relatively low wall height which allows access to most of the membrane 840 with an objective of a microscope, preferably a water immersible objective. Moreover, the low wall height of plate 845 allows access for a micro instrument, such as a micropipet, to contact single cells under view during or without active flexation. A pressure differential supply line 865 extends through the side of the body 805 and opens into the well 815 so that a pressure differential may be exerted on the underside of the membrane 840. In operation, it should be appreciated that the smaller diameter bore 820 in the bottom of the body 805 should be sealed. A base 870 may be secured to the bottom of the body 805 to improve the stability of the single well culture plate 800 on the stage of a microscope.

The clamping arrangement of the single well culture plate 800 as illustrated seals the well 815 but may not pretension the membrane 840 to the same degree as the previously discussed tongue/groove arrangement of the culture plate 10. If greater pretensioning of the membrane 840 is desired, then a similar tongue/groove arrangement may be incorporated into the single well culture plate design.

The shape of the wells in the culture plates 10 and 800 have been described as cylindrical. Such a description is only a matter of convenience, and so long as there is a proper seal between the base and the membrane, any of a variety of different shapes may be used in the culture plates. Furthermore, the culture plate 10 itself has been described as having a generally rectangular shape. This again is only a matter of convenience and the shape of the culture plate may be any of a variety of designs as the need arises. Additionally, while the culture plates 10 and 800 are described as having six wells and one well, respectively, it is entirely possible to utilize a different number of wells and still incorporate the features of this invention.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A cell culture plate comprising:
    a base having an upper surface and defining a base opening;
    a flexible membrane covering said base opening and a portion of said upper surface, said covered opening defining a cell culture surface; and
    a body engaged with said base such that said flexible membrane is fixed between said base and said body, wherein said body defines a body opening aligned with said base opening and includes a well wall extending from an upper surface of said body and surrounding said body opening, whereby said cell culture surface and said well wall define a well.

2. The cell culture plate as claimed in claim 1 wherein said base upper surface defines a groove surrounding said base opening and said body includes a tongue extending from a lower surface of said body, with said tongue matingly engaging with said groove thereby fixing said flexible member between said tongue and said groove.

3. The cell culture plate as claimed in claim 1 further comprising a spacer positioned between said base and said body, with said spacer adapted to maintain said body spaced apart from said base.

4. The cell culture plate as claimed in claim 3 wherein said spacer comprises a post and said flexible membrane defines an aperture, with said post extending through said aperture.

5. The cell culture plate as claimed in claim 4 wherein said post is integral with one of said body and said base, and said post is fixed to the other of said body and said base.

6. The cell culture plate as claimed in claim 1 wherein said base defines a plurality of base openings covered by said membrane and said body defines a plurality of body openings, with each said body opening axially aligned with one of said base openings, with each said body opening being surrounded by a well wall extending from said body upper surface and a tongue extending from said body lower surface, and with each said base opening being surrounded by a groove matingly engaged with one of said tongues.

7. The cell culture plate as claimed in claim 6 wherein said body further includes a side wall surrounding all of said well walls and at least one body rib extending between outer surfaces of a pair of said well walls and at least one body rib extending between an outer surface of one said well wall and said side wall.

8. The cell culture plate as claimed in claim 7 wherein said base further includes:

a plurality of support walls extending from a lower surface of said base, with each said support wall surrounding one of said base openings;

a base wall surrounding said support walls; and at least one rib extending between outer surfaces of a pair of said support walls and at least one rib extending between an outer surface of one said support wall and said base wall.

9. The cell culture plate as claimed in claim 1 wherein said membrane is formed from a silicone material.

10. A cell culture well comprising:

an annular member defining a chamber and a port in fluid communication with said chamber, said annular member having a wall, a top surface and a base;

a flexible membrane extending across said top surface; and a plate defining an opening, with said plate overlying said flexible member and attached to said annular member, wherein said port is configured to be connected to a pressure supply, such that when a pressure differential is provided from the pressure supply, said flexible membrane is stretched.

11. The cell culture well as claimed in claim 10 further comprising a sealing ring disposed in a groove in said top surface and a plurality of fasteners extending through said plate and into said top surface.

12. The cell culture well as claimed in claim 10 wherein said base defines an aperture aligned with said opening.

13. The cell culture well as claimed in claim 10 wherein when the pressure supply is a vacuum source and a negative pressure is provided, said flexible membrane is stretched downwardly.

14. The cell culture well as claimed in claim 10 wherein when the pressure supply is a positive pressure source and a positive pressure is applied, said flexible membrane is stretched upwardly.

15. A cell culture plate assembly comprising:

a cell culture plate having (i) a base having an upper surface and defining a base opening; (ii) a flexible membrane covering said base opening and a portion of said upper surface, with said covered opening defining a cell culture surface; and (iii) a body engaged with said base such that said flexible membrane is fixed between said base and said body, wherein said body defines a body opening aligned with said base opening and includes a well wall extending from an upper surface of said body and surrounding said body opening, whereby said cell culture surface and said well wall define a well; and a baseplate defining a recessed portion having a bottom surface with a central opening therethrough, with said cell culture plate sealingly fitted within said recessed portion, with said baseplate further defining a port and a passageway through said baseplate in fluid communication with said port and said central opening.

16. A cell culture plate assembly as claimed in claim 15 further comprising a gasket surrounding said cell culture plate, with said gasket sealingly fitted within said recessed portion.

17. A cell culture plate assembly as claimed in claim 16 wherein said baseplate defines a plurality of said recessed portions, and wherein a central opening defined in each recessed portion is equidistantly located from said port, with said assembly further comprising a plurality of said cell culture plates, each of which are sealingly fitted within one of said recessed portions.

18. The cell culture plate assembly as claimed in claim 15 further comprising a plurality of cell culture lids, with each said lid sized to fit over one of said cell culture plates.

19. The cell culture plate assembly as claimed in claim 15 wherein said port is configured to be connected to a pressure supply, such that said cell culture surface is stretched when a pressure differential is provided from the pressure supply.

20. The cell culture plate assembly as claimed in claim 19 wherein said cell culture surface is stretched downwardly when the pressure supply is a vacuum source and a negative pressure differential is provided.

21. A cell culture baseplate comprising a body defining a recessed portion having a bottom surface with a central opening therethrough, with said body further defining a port and a passageway through said body in fluid communication with said port and said central opening, wherein said recessed portion is configured to receive a cell culture plate and said port is configured to be coupled to a means for inducing a pressure change in said passageway and on an underside of the cell culture plate.

22. The baseplate as claimed in claim 21 wherein said body defines a plurality of said recessed portions and said central opening in each recessed portion is equidistantly located from said port.

* * * * *